(12) United States Patent
Imori

(10) Patent No.: US 9,676,127 B2
(45) Date of Patent: Jun. 13, 2017

(54) LANCET, METHOD FOR MANUFACTURING THE LANCET, AND MOLD FOR THE METHOD

(75) Inventor: Hirokazu Imori, Okayama (JP)

(73) Assignee: ASAHI POLYSLIDER COMPANY, LIMITED, Osaka (JP)

( * ) Notice: Subject to any disclaimer, the term of this patent is extended or adjusted under 35 U.S.C. 154(b) by 1118 days.

(21) Appl. No.: 13/500,389

(22) PCT Filed: Oct. 6, 2010

(86) PCT No.: PCT/JP2010/067558
§ 371 (c)(1),
(2), (4) Date: Sep. 25, 2012

(87) PCT Pub. No.: WO2011/043383
PCT Pub. Date: Apr. 14, 2011

(65) Prior Publication Data
US 2013/0012976 A1    Jan. 10, 2013

(30) Foreign Application Priority Data
Oct. 7, 2009    (JP) .................................. 2009-233426

(51) Int. Cl.
*A61B 17/14* (2006.01)
*B29C 45/00* (2006.01)
(Continued)

(52) U.S. Cl.
CPC .... *B29C 45/0046* (2013.01); *A61B 5/150022* (2013.01); *A61B 5/15142* (2013.01);
(Continued)

(58) Field of Classification Search
CPC . B29C 45/03; B29C 45/06; B29C 2045/0049; B29C 49/48; B29C 45/0046;
(Continued)

(56) References Cited

U.S. PATENT DOCUMENTS 3,358,689 A * 12/1967 Higgins ............... A61B 5/1405
  206/367
4,091,069 A *  5/1978 Allen ....................... 264/328.16
(Continued)

FOREIGN PATENT DOCUMENTS

JP         5-285127      11/1993
JP      2005-529704      10/2005

OTHER PUBLICATIONS

International Search Report issued Dec. 21, 2010 in International (PCT) Application No. PCT/JP2010/067558.
(Continued)

*Primary Examiner* — Jonathan Miles
*Assistant Examiner* — Kankindi Rwego
(74) *Attorney, Agent, or Firm* — Wenderoth, Lind & Ponack, L.L.P.

(57) ABSTRACT

There is provided a process of producing a lancet which suppresses curving (or flexing) of the front end portion of the pricking member.

In the production of a lancet by injection molding of a resin with a pricking member inserted in a mold, upon forming at least a portion of a lancet cap in which portion a molten resin supplied to the mold surrounds a front end portion of the pricking member, a mold is used which is configured such that at least a portion of the molten resin which forms said portion of the lancet cap flows along the front end portion including a leading end of the pricking member toward its leading end.

17 Claims, 7 Drawing Sheets

(51) Int. Cl.
*A61B 5/151* (2006.01)
*B29C 45/14* (2006.01)
*A61B 5/15* (2006.01)

(52) U.S. Cl.
CPC .. *A61B 5/150282* (2013.01); *A61B 5/150412* (2013.01); *A61B 5/150519* (2013.01); *A61B 5/150549* (2013.01); *A61B 5/150618* (2013.01); *B29C 45/14073* (2013.01); *B29C 45/14836* (2013.01); *A61B 5/1513* (2013.01); *B29C 45/14065* (2013.01)

(58) Field of Classification Search
CPC .......... B29C 45/14065; B29C 45/1634; B29C 2045/14122; B29C 2045/14147; B29C 2045/14155; B29C 33/42; B29C 2033/422; A61B 5/1411; A61B 5/150022; A61B 5/150282; A61B 5/150412; A61B 5/150519; A61B 5/150549; A61B 5/150618; A61B 5/15142; A61B 5/150259; A61B 5/150206; A61B 5/150274; A61B 5/150297; A61B 5/150312; A61B 5/15032
USPC ..................................................... 246/328.12
See application file for complete search history.

(56) References Cited

U.S. PATENT DOCUMENTS

| | | | | |
|---|---|---|---|---|
| 4,576,671 | A * | 3/1986 | Shimanaka | .................... 156/245 |
| 2004/0068282 | A1* | 4/2004 | Bicknell | .............. A61B 5/1411 606/181 |
| 2005/0240207 | A1* | 10/2005 | Marshall | .............. A61B 5/1411 606/181 |
| 2007/0293883 | A1* | 12/2007 | Horie | ............................ 606/181 |
| 2009/0115105 | A1* | 5/2009 | Czernik | ........... A61B 17/07207 264/328.9 |
| 2009/0299396 | A1 | 12/2009 | Nicholls | |

OTHER PUBLICATIONS

English translation of International Preliminary Report on Patentability issued May 8, 2012 in International (PCT) Application No. PCT/JP2010/067558.
Chinese Office Action issued Dec. 19, 2013 in corresponding Chinese Patent Application No. 201080045189.6, together with English translation thereof.
Chinese Search Report issued Dec. 13, 2013 in corresponding Chinese Patent Application No. 201080045189.6, together with English translation thereof.

* cited by examiner

LANCET, METHOD FOR MANUFACTURING THE LANCET, AND MOLD FOR THE METHOD

TECHNICAL FIELD

The present invention relates to a production (or manufacturing) process of a lancet as well as a lancet produced by such a process and a mold for that process. In the present description, the lancet means a device which comprises a pricking member having a sharp front end portion which injures a predetermined portion of a body and which is constructed such that the device is launched or ejected toward the predetermined portion so that the front end portion pricks the predetermined portion. Such device includes various lancets which are widely used for collecting a body fluid, particularly blood from the predetermined portion.

BACKGROUND ART

When blood is collected from a predetermined position of a body for the purpose of various tests, it sometimes happens that such position is injured by a member having a sharp front end portion so as to exudate the blood from that position. A device called a lancet is used for such injuring. For example, in order to measure a glucose concentration in blood, a fingertip, an ear lobe or a palm is injured so as to collect blood.

The lancet used for the blood collection generally comprises a lancet cap and a lancet body, which are formed integrally by means of a weakened portion between them, so that a pricking member (such as a needle) extends through that portion while straddling them.

Upon blood collecting, a rear end portion of the lancet body is inserted into an injector which ejects the lancet toward a predetermined position, so that the lancet is loaded on the injector. Then, the weakened portion is broken so as to remove the lancet cap from the lancet body, so that an front end portion of the pricking member is exposed from a front end portion of the lancet body. When such lancet body is ejected thereafter, such exposed front end portion instantaneously moves toward and sticks the predetermined position, that it pricks the predetermined position, and then returns back immediately.

Pricking as mentioned above is an operation to injure a body by means of a sharp member. Before carrying out pricking, people whose blood is collected have a kind of tension in that they would feel some pain, and just upon pricking, they feel some pain. It is desirable that such tension and pain are depressurized as much as possible. For such depressurizing, it is conceived that a finer needle is used as the pricking member. The finer needle is desirable from a viewpoint of depressurizing, but there comes up a problem in that such needle is readily bent due to its less rigidity.

The lancet as mentioned above is produced by an injection molding process wherein a molten resin is injected into a mold in which a pricking member is inserted beforehand followed by solidifying the injected resin. When the pricking member is finer, a force generated by means of inertia of the injected molten resin is applied to the pricking member supported in the mold, so that molding may be carried out while the pricking member is in its curved (or flexed) state. For example, it is possible that a front end portion of the pricking member is curved (or flexed).

In the case wherein the front end portion of the pricking member is curved (or flexed), it is possible that said portion is not in the condition wherein it is exposed straight from the end surface of a front end portion of the lancet body when the lancet cap is removed from the lancet body upon pricking. When an injector ejects such lancet body toward a predetermined position, the front end portion of the pricking member is to stick in the predetermined position obliquely as to such portion (in spite of an intention that it essentially pricks at a right angle or an angle close thereto). In this case, the direction along which the lancet body moves is not corresponding to the direction along which the front end portion of the pricking member pricks the predetermined position.

As a result, since the front end portion of the pricking member tries to move obliquely in the skin, smoothly moving of that portion in the skin becomes more difficult compared with a case in which the pricking member is not curved (or flexed), so that pain which is felt upon pricking is increased. Therefore, it is desirable that curving (flexing) of the pricking member, particularly an area around the front end portion thereof is suppressed.

In order to suppress the above mentioned curving (or flexing) of the pricking member, a production process of a lancet is proposed in which an outer peripheral portion of a lancet cap is thicker while a portion of the lancet cap close to a front end portion of the pricking member is thinner (see Patent Document 1 below).

As to the lancet produced by the above mentioned process, a portion between the front end portion of the pricking member and the outer peripheral portion is thin. Thus, in a mold with which such lancet is formed, its passage for a molten resin to be injected through a point corresponding to a leading end of the lancet cap is narrow in an area corresponding to such thin portion. It is said that as a result, a velocity of the molten resin which passes through such narrow area is tentatively lowered, so that the inertia of the injected resin is equalized, whereby a force which intends to curve the front end portion of the pricking member is relaxed.

However, in order to produce the same number of the lancet as conventional according to the above mentioned process, an injection pressure of the molten resin should be increased because the passage for the molten resin is narrow. In this case, the inertia of the injected molten resin becomes larger, so that there comes a problem in that the effect of curving suppression may be insufficient. On the other hand, when the injection pressure of the molten resin is reduced, it takes a longer time to fill the mold with the molten resin, so that there comes a problem in that the same number of the lancet cannot be produced.

Patent Document 1:
Japanese Patent Kohyo Publication No. 2005-529704

DISCLOSURE OF THE INVENTION

Problem to be Solved by the Invention

Therefore, it is desired that the above mentioned problems are suppressed as much as possible, so that a process of producing a lancet is provided wherein curving (or flexing) of the front end portion of the pricking member is further suppressed.

Means to Solve the Problem

The inventor studied the above mentioned problem extensively, and finally has found that the problem is solved by a process of producing a lancet by injection molding of a resin with a pricking member inserted in a mold as a forming tool (i.e. insert molding) wherein upon forming at least a portion of a lancet cap in which portion the molten resin supplied to the mold surrounds a front end portion of a pricking member (that is, a front end portion surrounding portion), a mold is configured such that at least a portion of the molten resin which forms said portion of the lancet cap "flows along the front end portion of the pricking member toward its leading end". It is noted that "at least a portion of the molten resin" is intended to mean that a whole of the molten resin which "flows along the front end portion of the pricking member toward its leading end" may form the front end portion surrounding portion or a portion of such molten resin may form the front end portion surrounding portion.

More specifically, the above mentioned "flows along the front end portion of the pricking member toward its leading end" is carried out by providing the mold which is configured such that said "at least a portion of the molten resin" flows from a lateral position beside any point of the front end portion of the pricking member (i.e. side position) toward the pricking member while a gas (usually air) present in a cavity of the mold which is to be filled with said "at least a portion of the molten resin" is pushed out of the mold through an opening located through a mold wall positioned in front of the leading end of the inserted pricking member. Therefore, in the process for the production of the lancet according to the present invention, said "at least a portion of the molten resin" flows along at least a portion of the front end portion which includes the leading end of the pricking member toward the leading end.

The above mentioned "any point of the front end portion of the pricking member" is not particularly limited as long as such point is located at somewhere of the front end portion of the pricking member. Such point may be the tail end of the front end portion, or it may be the front-most end of the front end portion (therefore, the front-most end of the pricking member). Such point is preferably between the leading end and the rear-most end of the front end portion (that is, any point which is located behind the front-most end of the front end portion and in front of the tailing end of the front end portion), and more preferably located at any point which is located on the front side of the middle point between the leading end and the rear-most end of the front end portion. Such "any point" may be any point located on an outer periphery around the pricking member, or may be in a ling form as a portion of the outer periphery or a whole of the outer periphery (usually a circle). Alternatively, it may be in a plane form wherein such line is extended along a longitudinal direction of the pricking member by a predetermined length. In a further embodiment, it may be in a line-like form wherein the above mentioned points are located along the longitudinal direction of the pricking member over a predetermined length.

The lateral position of the above mentioned "any point" is any point located on an outside from the outer periphery of the pricking member (for example, a point on a circle of which center corresponds to the pricking member so as to encompass the pricking member) which outside is laterally separated from said any point of the pricking member by a space. When such any point is in a dot form, the "lateral position" may also be in a dot form. When such any point is in a line form, the "lateral position" is also in a line form. When such any point is in a plane form, the "lateral position" is also in a plane form.

It is preferable that a plurality of the above mentioned "any point of the front end portion of the pricking member" are present. It is preferable that each stream of the molten resin goes from the lateral position toward the front end portion of the pricking member, and then goes as a stream that "flows along the front end portion of the pricking member toward a leading end of the front end portion" wherein those streams are in a symmetric condition as to the pricking member. That is, assuming a cross section of the pricking member perpendicular to the longitudinal direction of the pricking member as a point or a very small circle, the streams are in a point symmetry condition as to such point or vary small circle and/or in a line symmetry condition as to a straight line which passes such a point or very small circle. It is noted that as to "the streams are in the symmetric condition", the directions and amounts of the streams are particularly to be considered. Also, it is more preferable that each of the streams is equalized at any position around the pricking member. For example, the streams of the molten resin toward the leading end of the pricking member flow ahead evenly around the pricking member. In the most preferable embodiment, the resin which flows around the pricking member is equivalent along a circumferential direction of the pricking member at any point along the longitudinal direction of the pricking member.

In order to achieve the above mentioned symmetrical flow, for example, it is preferable that above mentioned "any point of the front end portion of the pricking member" is located in a symmetric condition around the pricking member. For example, the above mentioned "any point of the front end portion of the pricking member" is provided so as to face each other through the pricking member (that is, at an angle of every 180° around the pricking member), or provided at an even angle (for example, every 120°, every 90° or every 60°) around the pricking member. In a particularly preferable embodiment, the above mentioned "any point of the front end portion of the pricking member" is present around a whole periphery of the pricking member. That is, "any point of the front end portion of the pricking member" is continuously (therefore, infinitely) present.

In the first aspect, the present invention provides a process for the production of a lancet by injecting a molten resin into a mold including a pricking member inserted therein beforehand followed by solidifying the resin, which process is characterized in that the lancet comprises a lancet body and a lancet cap which are integrated with a weakened portion, the pricking member which extends in the lancet body and the lancet cap, the pricking member comprises, as its portion, a front end portion which extends in the lancet cap (which portion protrudes from a front end of the lancet body upon using the lancet), the front end portion of the pricking member comprises, at its front end portion, a sharp leading end which sticks a predetermined portion, and the mold to be used comprises a cavity forming a resin passage which is formed so as to make a portion of the molten resin supplied to the mold flow along the front end portion toward its leading end (therefore, so as to substantially prevent said portion of the molten resin from flowing from the leading end backward and toward a rear of the front end portion), (in consequence, said portion of the molten resin forms at least a portion of a front end portion surrounding portion of the lancet cap which encloses the front end portion of the pricking member).

It is noted in the present description that as to the lancet having the pricking member which extends in the lancet cap and the lancet body which are connected integrally together through the weakened portion, the "front end portion of the pricking member" is intended to mean a portion of the pricking member which portion protrudes from a front end surface of the lancet body when the weakened portion is broken and the lancet body is separated from the lancet body for the purpose of pricking. Also, the "leading end of the front end portion" is intended to mean a front-most end (which can substantially be regarded as a point) of the front end portion which is a portion of the pricking member.

In a preferable embodiment of the process according to the present invention, the mold to be used includes a molten resin passage which is configured such that the molten resin flows toward a lateral position beside the front end portion of the pricking member, and then changes its flowing direction so as to flow forward along the front end portion of the pricking member. In one embodiment, the mold is configured such that the molten resin flows from a lateral position beside the pricking member toward the pricking member substantially perpendicular to the front end portion, and then changes its flowing direction so as to flow forward along the front end portion of the pricking member. In other embodiment, the mold is configured such that the molten resin flows from a lateral position beside the pricking member obliquely toward the front end portion of the pricking member, and then changes its flowing direction so as to flow forward along the front end portion of the pricking member. A further embodiment may employ a combination of the above mentioned embodiments. It is noted that the change of the flowing direction happens not like in a polygonal line, but like a curved line wherein the flowing direction in fact gradually changes. It should be understood that the first flow direction of the molten resin changes to the final flow direction of the molten resin as described in the above.

In the second aspect, the present invention provides a lancet which is produced by the process for the production of the lancet according to the present invention as described above. This lancet is characterized in that a portion of the lancet cap which portion surrounds the front end portion of the pricking member (i.e. the front end portion surrounding portion) includes a convex portion which protrudes forward so as to define cavities on the both sides and in front of the front end portion surrounding portion and encloses at least the leading end of the front end portion of the pricking member. The cavities may pass through vertically as to the lancet, or the cavities may have a wall, preferably a thin wall, for example a layered or film potion as bottoms of the cavities.

In the third aspect, the present invention provides a mold which is used in the process for the production of the lancet according to the present invention as described above. The mold has a wall as a blocking member which is located between a gate and the leading end of the pricking member on a line connecting them, so that the mold is configured such that the molten resin which is supplied through the gate into a mold cavity is prevented from flowing directly toward the leading end of the pricking member. It is noted that the above and below explanations as to the process for the production of the lancet according to the present invention are applicable when relevant.

Effects of the Invention

In the production process according to the present invention, a portion of the molten resin supplied to the mold flows from a lateral position beside the front end portion toward the front end portion, and then flows along the front end portion and substantially passes the leading end finally up to its front. That is, such molten resin flows first near the leading end of the front end portion from its near side and then flows in the vicinity of the leading end. In the mold, since the pricking member is generally supported at two points (points from the both ends of the pricking member inside by ⅓ to ¼ of the length of the pricking member) so that a length between a fulcrum point and an operation point is large, a large moment is acted on the leading end of the pricking member even though a small force is applied to the leading end. (It is noted that in the drawings referred to below, holes 52 and 54 are shown which are formed by the presence of support pins which function to support the pricking member.)

Therefore, when the leading end of the pricking member is located as downstream as possible as to the molten resin flow, the molten resin has already surrounded a portion of the front end portion near the leading end before the molten resin reaches the leading end of the pricking member, so that the fulcrum point at which the pricking member is supported is shifted forward to the leading end side, whereby a moment acted to the leading end is greatly reduced. In addition, the inertia of the molten resin flow becomes smaller in its more downstream, i.e. nearer the leading end. As a result of those, the moment acted on the leading end of the pricking member and the inertia of the molten resin become smaller in the present invention, so that the occurrence of curving or flexing of the front end portion of the pricking member is suppressed. Considering such effect, the present invention is particularly effective for the production of a lancet wherein a diameter of the pricking member is small. For example, when a stainless steel needle is used as the pricking member, the production process according to the present invention is advantageous in the case wherein the diameter of the needle is 0.4 mm or smaller, for example 0.32 mm or smaller, and particularly advantageous in the case wherein the diameter of the needle is 0.3 mm or smaller, especially 0.2 mm or smaller.

EXPLANATION OF THE REFERENCE NUMBERS

10: lancet, 12: lancet body, 14: lancet cap,
16: weakened portion, 18: concave portion,
20: pricking member, 22: front end portion,
24: leading end, 26: rear end portion,
30: leading end of lancet, 30': gate of mold,
32: front portion, 34: rear portion,
36: front end portion surrounding portion,
38: connection portion, 44: front cavity,
46: side cavity, 48: side cavity,
50: convex portion, 60: mold,
62: sliding back stopping pin, 64: pushing out pin,
66: pushing out pin, 68: pushing out pin,
70: upper mold half, 72: support pin, 74: support pin,
80: lower mold half, 82: pin, 84: pin,
86: ejection opening

EMBODIMENTS TO CARRY OUT THE INVENTION

Figure 1:
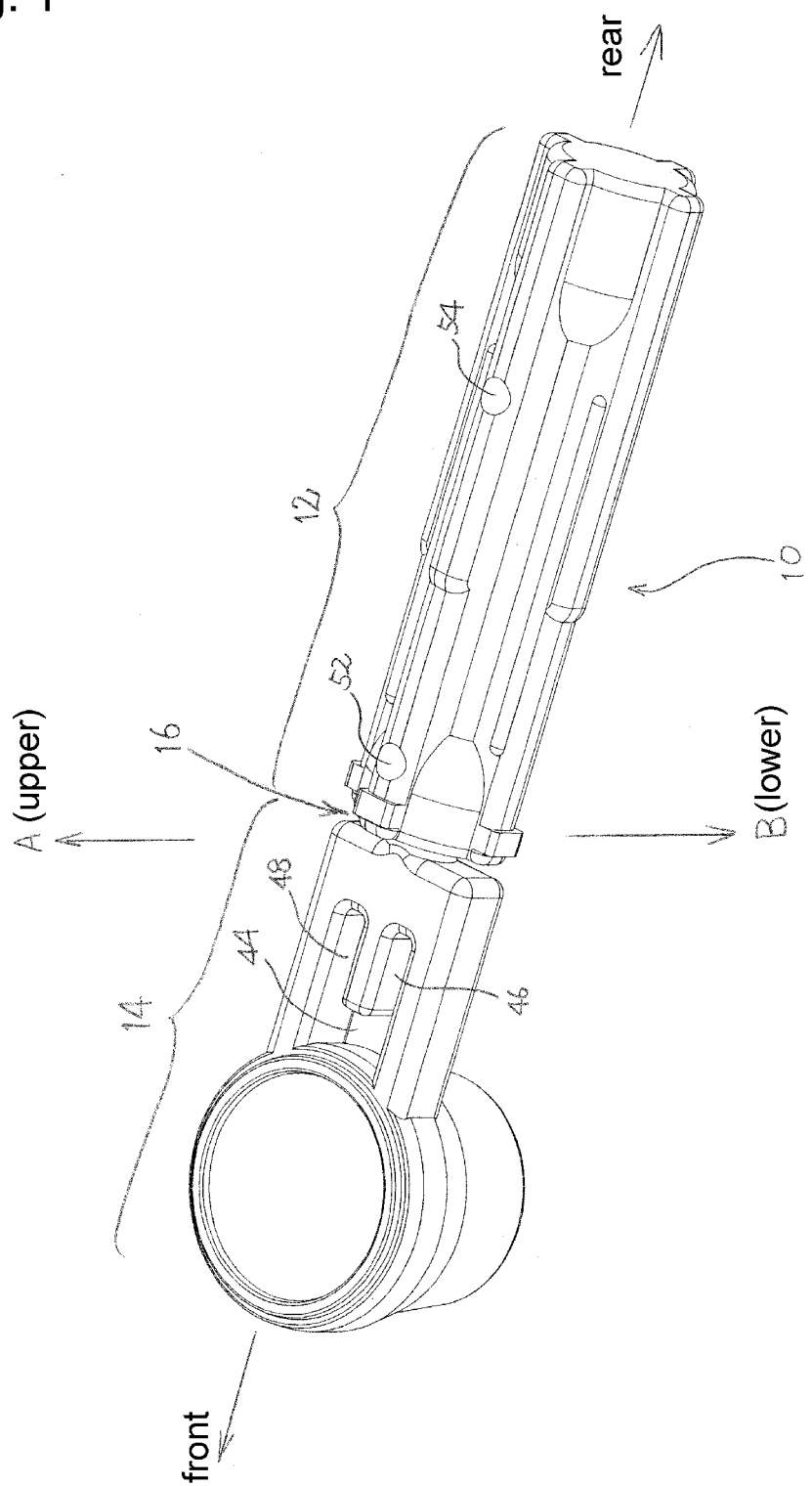
FIG. 1 schematically shows a perspective view of a lancet according to the present invention when viewing it from its above obliquely.
Figure 2:
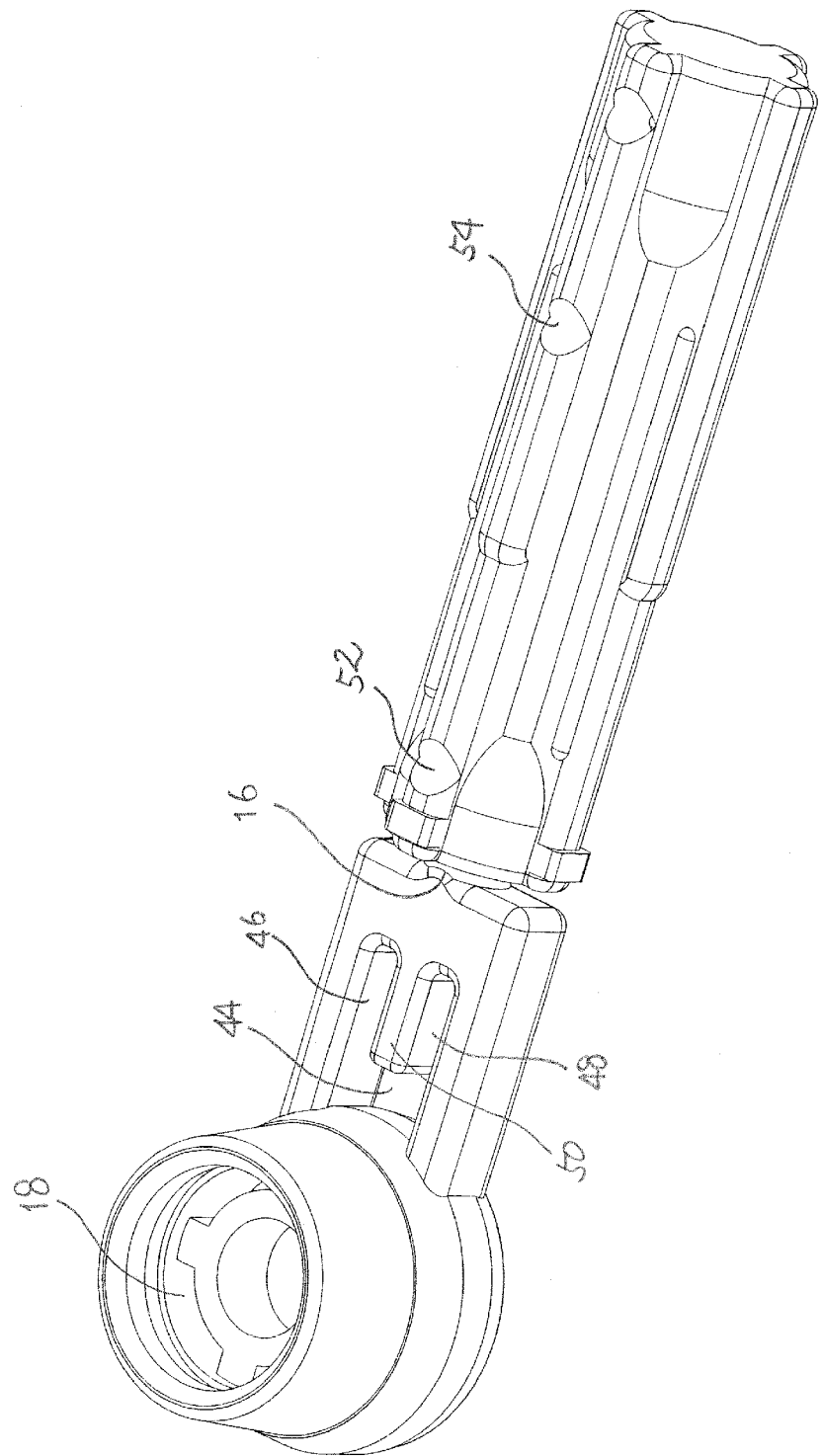
FIG. 2 schematically shows a perspective view of the lancet of FIG. 1 while it is turned upside down.

The lancet of the present invention which is produced by the production process according to the present invention is shown in its perspective view in FIG. 1 when it is viewed from its oblique above and also in FIG. 2 when it is turned upside down. The lancet 10 comprises a lancet body 12 and a lancet cap 14, which are connected integrally by means of a weakened portion 16 which is located between them. The pricking member strides the lancet body 12 and the lancet cap 14, and a portion of the pricking member which extends in front of the weakened portion corresponds to the front end portion.

The shown lancet comprises a concave portion 18 in a front portion of the lancet cap, and a front end portion of the lancet body 12 with the leading end of the front end portion of the pricking member protruding from its end surface is adapted to fit into the concave portion 18. By means of the front end portion of the lancet body thus fitting into the concave potion, the protruding front end portion of the pricking member is substantially insulated, so that the spent lancet is can be disposed without carelessly touching the front end portion of the pricking member.

Figure 3:
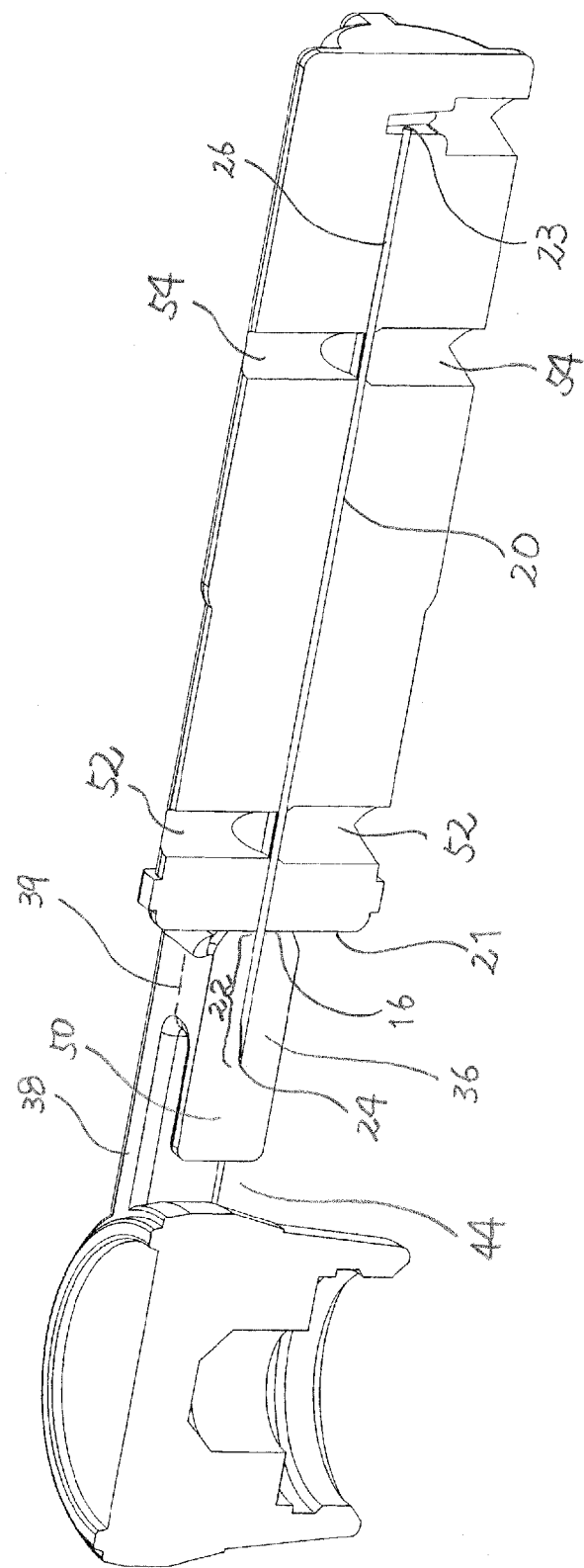
FIG. 3 schematically shows the lancet of FIG. 1 according to the present invention while its near side half is cut away (except that a whole of the pricking member is shown).
Figure 4:
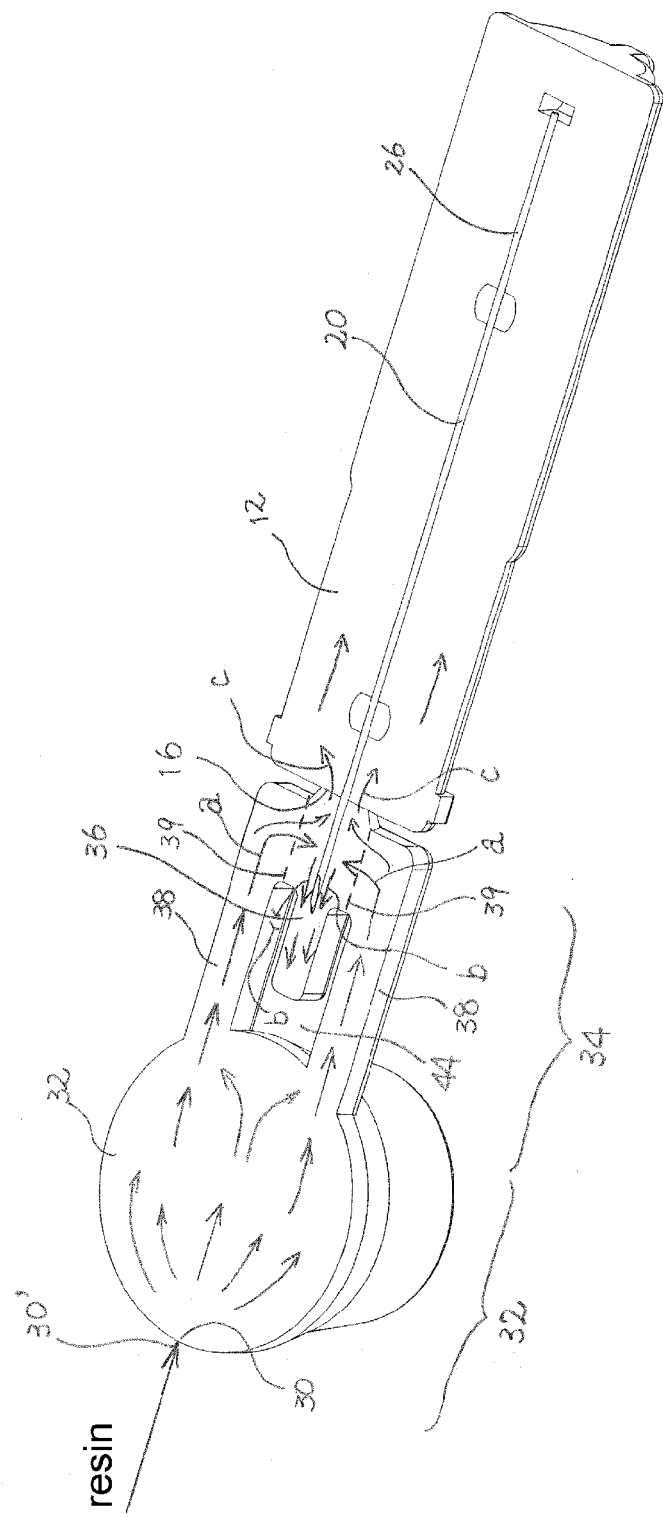
FIG. 4 schematically shows the lancet of FIG. 1 according to the present invention while its near half is cut away when the lancet is cut along a plane including the pricking member (which plane is perpendicular to the cut away plane in FIG. 3) (except that a whole of the pricking member is shown).

In FIG. 3, the lancet according to the present invention shown in FIG. 1 is schematically shown in a perspective view with its near side half cut away except that the pricking member is shown in whole. In FIG. 4, the lancet according to the present invention shown in FIG. 1 is schematically shown in a perspective view with its upper side half cut away when the lancet is cut along a plane which includes the pricking member (and which is perpendicular to the cut away plane in FIG. 3) except that the pricking member is shown in whole.

As readily seen, a portion of the pricking member 20 protruding forward from the front end surface 21 of the lancet body 12 in which the pricking member extends while striding the lancet body 12 and the lancet cap 14 corresponds to the front end portion 22 of the pricking member 20. Upon pricking, when the lancet cap 14 is removed by breaking the weakened portion 16 by means of twisting-off, the portion which protrudes from the front end surface of the lancet body corresponds to the front end portion 22. The leading end 24 of the front end portion 22 corresponds to the front-most end of the pricking member.

The mold which is used in the process for the production of the lancet according to the present invention will be explained below with reference to the lancet which is to be produced. It is noted that the produced lancet corresponds to the cavity of the mold, and the exposed surfaces of the produced lancet correspond to the walls of the cavity of the mold. Since the basic concept of the present invention resides in the flow of the molten resin, it is convenient to refer to the lancet to be produced.

Figure 5:
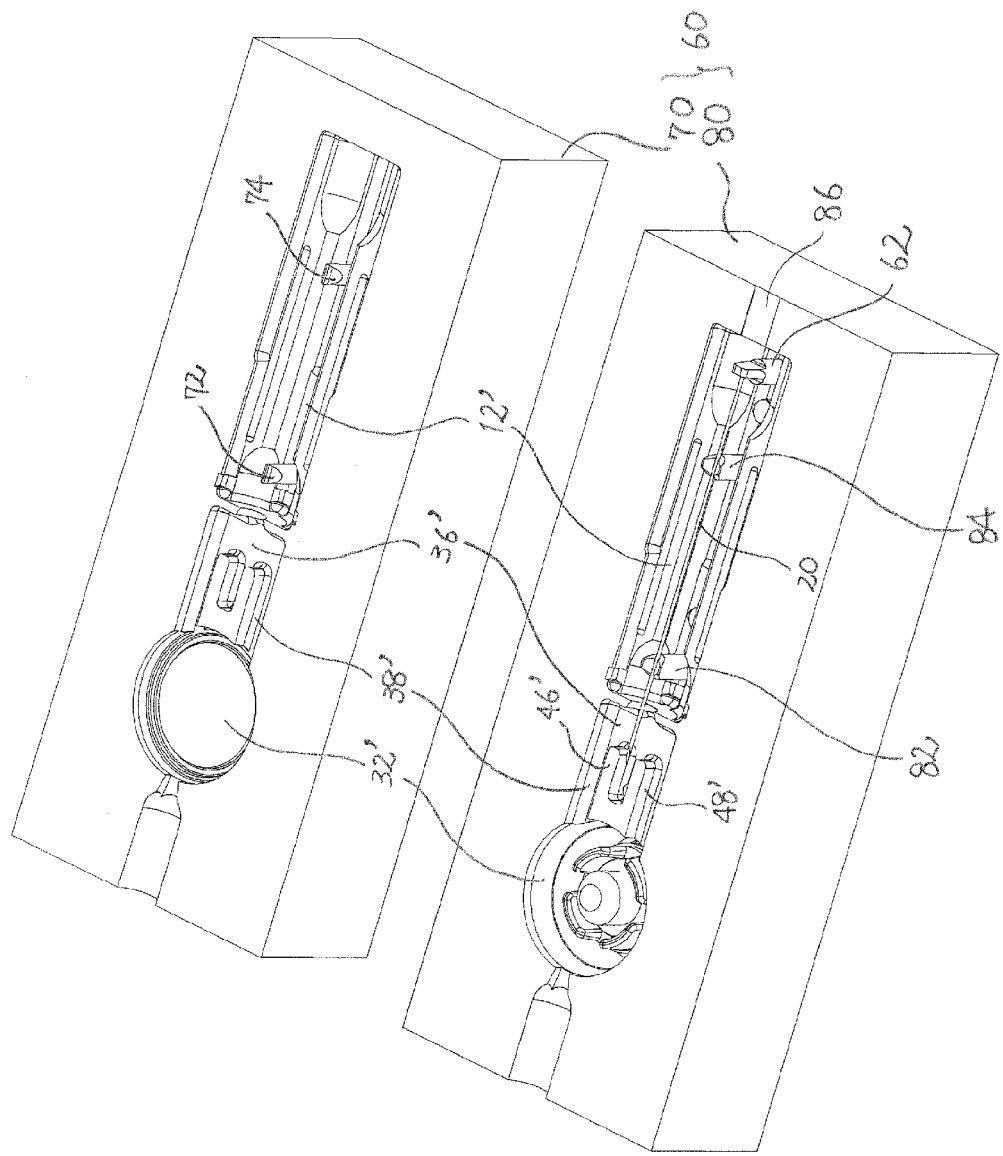
FIG. 5 schematically shows a perspective view of a mold in its open state which is used when the lancet according to the present invention is formed.
Figure 6:
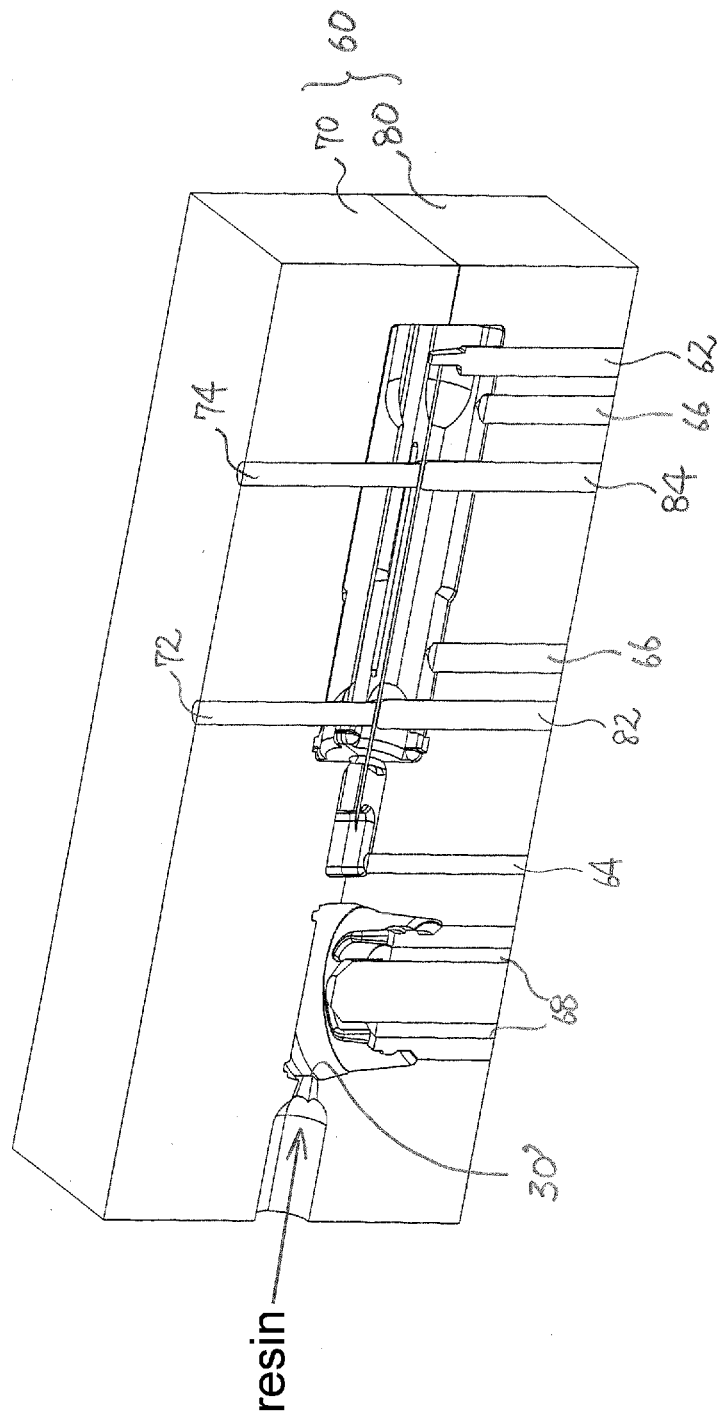
FIG. 6 schematically shows a perspective view of the mold of FIG. 5 in its closed state, namely in the state wherein an upper mold half and a lower mold half are fastened (except that a near half of the mold is cut away).

In order to explain the present invention in detail, one example of the mold for the production of the lancet is shown FIGS. 5 and 6. FIG. 5 schematically shows the mold in its perspective view while it is opened wherein the mold is composed of an upper mold half 70 and a lower mold half 80. The pricking member 20 is inserted between these mold halves as shown in FIG. 5, and a molten resin is injected in the condition wherein these mold halves are fastened while the upper surfaces of them are joined together, so that the lancet is injection-molded. In FIG. 6, the mold which is formed together by fastening the halves is schematically shown in a perspective view while a near half of the mold is cut away.

When the shown mold is used, the pricking member 20 is supported by support pins 72 and 74 on the upper mold half side as well as support pins 82 and 84 on the lower mold halve side, and a pin 62 supports the rear end 23 of the pricking member which functions as a backward movement stopper of the pricking member. The pin 62 has a surface which the end surface 23 abuts. As a result, in the condition wherein the rear end 23 of the pricking member abuts the pin 62, the backward movement of the pricking member is prevented even when a backward force is applied to the pricking member 20.

Upon carrying out the production process of the lancet according to the present invention, the molten resin is supplied into the cavity of the mold as shown with the arrows (in which the pricking member is supported beforehand as mentioned above) through a point 30' of the mold which corresponds to a leading end 30 of the lancet (see FIGS. 4 and 6). That is, that point 30' functions as a gate. A cavity which corresponds to a portion which defines the front portion 32 of the lancet cap 14, particularly the concave portion 18 (see FIG. 2) is first filled, and then a cavity which corresponds to a portion which defines the rear portion 34 of the lancet cap is filled.

By means of the latter cavity filling as mentioned above, the front end portion of the pricking member is enclosed by the resin, so that the front end portion surrounding portion 36 and the connection portions 38 bridging the portion 36 and the front portion 32 are formed (see FIG. 4, borders between the front end portion surrounding portion 36 and the connection portion 38 are shown with broken lines 39). As shown with arrows in FIG. 4, the resin fills the cavity 32' which forms the front portion 32, and then fills the cavity 38' which forms the connection portions 38. Thereafter, a portion of the resin fills the cavity 36' which forms the front end portion surrounding portion 36, and the other portion of the resin fills the cavity 12' which forms the lancet body 12. The flows of the resin as mentioned above are schematically shown in the arrows in FIG. 4.

What is particularly noted is in that the molten resin flows from a lateral position beside the pricking member toward the front end portion thereof (see arrows "a"), and then a portion of the molten resin flows along the front end portion 22 of the pricking member toward its leading end 24 (see arrows "b") while the balance of the molten resin flows toward the rear end 26 of the pricking member so as to form the lancet body (see arrows "c"). The present invention resides in the flows of the molten resin shown with arrows "a" and "b".

As readily seen from FIG. 4, the molten resin supplied to the mold flows through cavities which form the connection portions 38, and then a portion of the resin flows along the pricking member toward its leading end 24 and the other portion of the molten resin flows along the pricking member toward its rear end 26. That is, the molten resin is divided into a portion flowing forward and a portion flowing backward. The portion flowing backward fills the cavity which forms a portion of the rear portions of the front end portion surrounding portion 36 and then fills the cavities which form the weakened portion 16 and the lancet body 12.

It is noted that gas which has been present in the cavities before the injection is discharged out by the molten resin from the mold through a gap (not shown because it is narrow) between a push-out pin 64 located in front of the leading end of the pricking member and a peripheral hole wall around the pin 64 (which is used for the removal of the lancet after molding), gaps (not shown because they are narrow) between the support pins (72, 74, 82 and 84) and peripheral hole walls around the pins, a gap (not shown because it is narrow) between the pin 62 and a peripheral hole wall around the pin, a gap (not shown because it is narrow) between a push-out pin 66 (which is used for the removal of the lancet after molding) and a peripheral hole wall around the pin, and an exhaust opening 86 which is provided in the rear end portion 26 in the mold.

As readily seen, the gap between the push-out pin 64 (which is used for the removal of the lancet after molding) and the peripheral hole wall around the pin functions an opening provided in the wall of the mold which is located in front of the leading end of the pricking member, so that the gas (usually, air) present in the cavity of the mold is pushed out through the gap which cavity is to be filled by the above mentioned "at least a portion of the molten resin".

Figure 7:
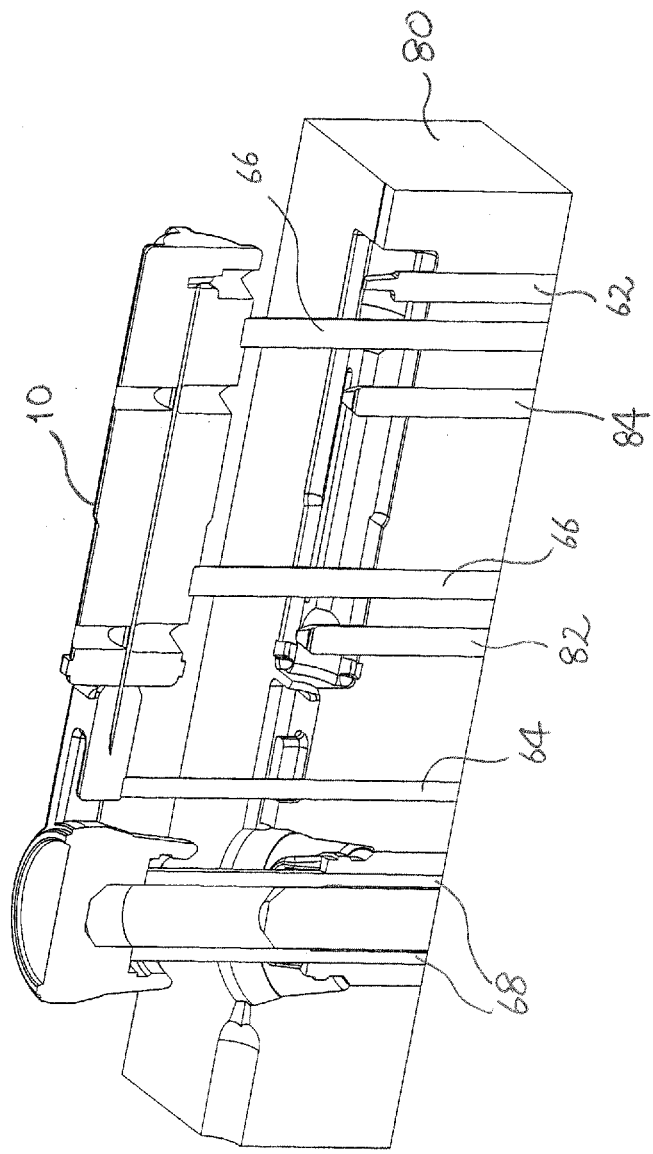
FIG. 7 schematically shows a lancet in a perspective view which is taken out of a lower mold half after injection molding of the lancet with using the mold shown in FIG. 5 and opening the mold (except that a near halves of the lancet and the mold are cut away).

It is noted that the gas in the cavity which corresponds to the front portion 32 of the lancet cap is pushed out through the gap (not shown) between push-put pins 68 (which is used for the removal of the lancet after molding) and peripheral hole walls around the pins. Also, it is noted that the lancet is schematically shown in FIG. 7 which is pushed out from the lower mold half by the push-out pins while opening the mold after molding.

In the production process according to the present invention, the molten resin flow from any lateral position beside the front end portion toward the front end portion after filling the cavity which form the connection portion. In the embodiment shown in FIG. 4, referring to the arrows, the molten resin flows from a near side and a far side of the front end portion 22 of the pricking member toward the pricking member over a relatively long length, so that such flowing corresponds to "any point of the front end portion of the pricking member" in the form of a line on the either side over some length of the pricking member. A portion of the resin which has flowed as described above flows along the front end portion toward its leading end to form the front portion of the front end portion surrounding portion 36 while the other portion flows along the front end portion toward its rear end 26 to form the rear portion of the front end portion surrounding portion 36 as well as the weakened portion and the lancet body 12.

As readily seen, the arrows are shown in FIG. 4 such that the molten resin flows from the near side lateral position and the far side lateral position (that is, from two points) toward the front end portion, and the flow of the molten resin is not limited to the embodiment shown with the arrows as long as the molten resin flows from the lateral position(s) around the front end portion of the pricking member equiangularly toward the front end portion. For example, in place of flowing toward the front end portion from every 180° lateral position (that is, from two points), the molten resin may flow from every 90° lateral position (that is, from four points) or from every any other equal degree lateral position. More preferably, the "lateral position beside any point of the front end portion of the pricking member" is not in the form of a dot, but in the form of a line. For example, such line may be in the form of an arc having a certain length provided equiangularly around the front end portion. Most preferably, the molten resin flows toward the front end portion from a whole periphery laterally spaced from the outside of the front end portion.

Further, the "lateral position beside any point of the front end portion of the pricking member" preferably extends over a certain length along the longitudinal direction of the front end portion. In such case, such position is in the form of a line or plane. In a particularly preferred embodiment, such position is in an annular form which is laterally spaced from and over a certain length along the front end portion.

In one embodiment, the mold which is used in the production process according to the present invention has a blocking member in a front portion of the cavity which forms a resin portion surrounding the front end portion of the pricking member (that is, the front end portion surrounding portion) and the blocking member is adapted to prevent the molten resin injected through an inlet, that is, the gate into the cavity of the mold from flowing directly toward the leading end of the pricking member. Specifically, such blocking member is provided as described below.

When the lancet is produced, a gate is generally provided at a point which corresponds to a center of a leading end of the lancet cap to be formed, and the molten resin is injected through the gate 30'. The pricking member inserted in the cavity of the mold is supported in the center of the cavity along the longitudinal direction of the cavity, so that the leading end 24 of the front end portion 22 of the supported pricking member is facing to the gate through a space. Therefore, it is sufficient that the blocking member is a partition which is positioned between the gate 30' and the leading end 24 of the front end portion. That is, the blocking member should be present on a straight line which connects the gate 30' and the leading end 24. Therefore, in one embodiment, the mold of the present invention has a wall as the blocking member which is provided on a line connecting the gate and the leading end of the pricking member.

Since the gate and the leading end can substantially be regarded to be like points, the partition is in principle able to block the molten resin injected through the gate so as to prevent the resin from directly flowing toward the leading end of the pricking member even though a width of the partition, that is, a length of the partition along a direction perpendicular to the longitudinal direction of the pricking member is not so long. However, since there is a resin stream which bypasses the partition toward the leading end, it is preferable that the partition has a certain length of the width.

When the lancet shown in FIG. 4 is produced, the mold to be used is adapted to form the cavity 44 in front of the front end portion surrounding portion 36 by providing a blocking member 44' in front of the cavity which forms the front end portion surrounding portion 36. In order to minimize an amount of the molten resin which flows around the blocking member and flows directly toward the leading end of the pricking member, the mold is adapted to further form the cavities 44 and 46 beside the front end portion surrounding portion 36. That is, blocking members 46' and 48' are provided in the mold so as to form the cavities 46 and 48.

Namely, in the shown embodiment, a mold is used in which the blocking member is provided so as to define a cavity of which front and both sides are closed around a portion of the front end portion of the pricking member which portion includes the leading end thereof. Only a rear portion and its both side portions are opened in such cavity, so that the molten resin gets into the cavity through its rear portion and/or the sides thereof and then flows along a portion of the front end portion of the pricking member toward its leading end.

By providing the blocking member as mentioned above, a portion of the lancet cap which encloses the front end portion of the pricking member (that is, the front end portion surrounding portion) defines the cavities 46 and 48 on the both sides of such front end portion surrounding portion as well as the cavity 44 in front of such portion, and the front end portion surrounding portion is characterized by comprising the convex portion 50 which protrudes forward and encloses at least the leading end of the front end portion of the pricking member. It is noted that those cavities may be those which penetrates vertically through the lancet as shown in the drawings.

In other embodiment, the cavities may have thin walls as their bottoms, that is, they may have thin films which close openings of such penetrating cavities at their ends. When the connection portions and the front end portion surrounding portions are connected with such walls, the positional relationship between the connection portions and the front end portion surrounding portion becomes firmer, so that the shape of the lancet cap becomes stable and careless breakage of the weakened portion is prevented. It is of course that the walls may be used for indicating product numbers thereon.

INDUSTRIAL APPLICABILITY

As to the lancet production process according to the present invention and the lancet produced by such process, known matters as to the known lancet production process and the lancet produced by the process can be applied except the above mentioned matters (that is, the concept according to the present invention in which the molten resin flows along the front end portion of the pricking member toward its leading end as well as the matters related such concept), and therefore explanations as to such known matters are omitted. For example, the known matters can be applied as to the materials used for the lancet, the known matters as to the pricking members, the general production process of the lancet and the like can be applied.

Therefore, when the technical matters according to the present invention is combined with the known matters as to the lancet, a lancet is produced with further less occurrence of bending in the front end portion. It is noted that the present invention can be applied not only to the shown lancet, but also it can be applied to various lancets in which the front end portion of the pricking member is enclosed with a resin.

It is noted that as to the terms "front" and "rear" which indicate directions, the direction along which the lancet moves for pricking is indicated with the term "front" and its opposite direction is indicated with the term "rear". Also, the term "upper" indicates the direction from the shown lancet toward its above in FIG. 1 (the direction of arrow A), and its opposite direction is indicated with the term "lower" (the direction of arrow B).

The present application claims a priority under Paris Convention or other relevant priority under a law in the state where the present application is filed based on Japanese Patent Application No. 2009-233426 filed on Oct. 7, 2009 (Title of Invention: Production Process of Lancet), and all of the contents of the Japanese Application form a portion of the present description.

The invention claimed is:

1. A process of producing a lancet by injection molding of a resin with a pricking member inserted in a mold, the process of producing a lancet comprising:
   supplying molten resin to the mold; and
   forming, with the mold and the molten resin, a lancet cap of the lancet, wherein
   the mold to be used in the forming is formed such that upon the forming of the lancet cap, at least a portion of the molten resin supplied to the mold surrounds a front end portion of the pricking member that includes a leading end of the pricking member, so as to make the at least a portion of the molten resin flow, in a second direction opposite to a first direction in which the molten resin is supplied to the mold, along the front end portion toward the leading end of the pricking member, the leading end being an end of the pricking member closest to where the molten resin is supplied to the mold.

2. The process of producing a lancet according to claim 1, wherein
   a cavity of the mold is configured such that the at least a portion of the molten resin flows from a lateral position beside any point of the front end portion of the pricking member toward the leading end of the pricking member while a gas present in the cavity of the mold, which cavity is to be filled with the at least a portion of the molten resin, is pushed out of the mold by the molten resin via an opening which is positioned through a wall in front of the leading end of the inserted pricking member.

3. The process of producing a lancet according to claim 1, wherein
   any point of the front end portion of the pricking member is a point on a leading end side from a middle point between the leading end of the front end portion and a rear-most end of the front end portion.

4. The process of producing a lancet according to claim 1, wherein
   any point of the front end portion of the pricking member is in a line as a whole of an outer periphery of the pricking member, or a plane like wherein such line extends along a longitudinal direction of the pricking member over a predetermined length.

5. The process of producing a lancet according to claim 2, wherein
   the lateral position beside said any point of the front end portion of the pricking member is located outside the pricking member.

6. The process of producing a lancet according to claim 2, wherein
   said any point of the front end portion of the pricking member includes at least one point of a plurality of points located symmetrically around the pricking member.

7. The process of producing a lancet according to claim 2, wherein
   said any point of the front end portion of the pricking member is present continuously over a whole of a periphery of the pricking member.

8. A process of producing a lancet by injecting a molten resin into a mold in which a pricking member is inserted, followed by solidifying the resin, wherein the lancet comprises a lancet body and a lancet cap which are integrated with a weakened portion, the pricking member extends in the lancet body and the lancet cap, the pricking member comprises a front end portion which extends in the lancet cap, the front end portion of the pricking member comprises a sharp leading end which sticks a predetermined portion, and the mold to be used comprises a cavity forming a resin passage which is formed so as to make a portion of the molten resin supplied to the mold flow, in a second direction opposite to a first direction in which the molten resin is injected into the mold, along the front end portion toward the sharp leading end of the pricking member, the sharp leading end being an end of the pricking member closest to where the molten resin is injected into the mold.

9. The process of producing a lancet according to claim 8, wherein the mold to be used includes the resin passage which is configured such that the molten resin flows toward a lateral position beside the front end portion of the pricking member, and then a flowing direction of the molten resin changes to the second direction so as to flow forward along the front end portion of the pricking member.

10. The process of producing a lancet according to claim 8 wherein the mold to be used is formed so as to make at least a portion of the molten resin which forms the lancet cap flow along the front end portion, including the sharp leading end of the pricking member, toward the sharp leading end of the pricking member.

11. The process of producing a lancet according to claim 8, wherein the mold comprises a blocking member for the molten resin in front of the sharp leading end of the front end portion of the pricking member.

12. A lancet produced by the process of producing a lancet of claim 1, wherein the lancet cap of the lancet includes a front end portion surrounding portion which surrounds the front end portion of the pricking member, and comprises a convex portion protruding forward, the convex portion defines cavities in front of and on both sides of the front end portion and the convex portion encloses at least the leading end of the front end portion of the pricking member, such that the at least a portion of the molten resin flows in the second direction along the front end portion toward the leading end of the pricking member.

13. The lancet according to claim 12, wherein the cavities are spaces located perpendicularly in the lancet.

14. The lancet according to claim 12, wherein the cavities comprise layer portions which close one side openings of the cavities which are located perpendicularly in the lancet.

15. The lancet according to claim 12, further comprising, as the pricking member, a needle made of a stainless steel of which diameter is 0.3 mm or less.

16. A mold which is used for a process of producing a lancet, the mold comprising:

a wall as a blocking member which is located between a gate and a leading end of a pricking member on a line connecting them, so that the mold is configured such that a molten resin which is supplied through the gate into a mold cavity of the mold is prevented from flowing directly toward the leading end of the pricking member, wherein upon forming at least a portion of a lancet cap of the lancet in which portion the molten resin supplied to the mold surrounds a front end portion of the pricking member that includes the leading end, the mold is formed so as to make at least a portion of the molten resin which forms said portion of the lancet cap flow, in a second direction opposite to a first direction in which the molten resin is supplied through the gate, along the front end portion toward the leading end of the pricking member, the leading end being an end of the pricking member closest to the gate of the mold.

17. The process of producing a lancet according to claim 1, wherein the forming of the lancet cap includes forming a front portion of the lancet cap, a front end portion supporting portion of the lancet cap, and a plurality of connection portions of the lancet cap, the plurality of connection portions bridging the front portion and the front end portion supporting portion.

* * * * *